United States Patent [19]

Horwell

[11] Patent Number: 4,677,122
[45] Date of Patent: Jun. 30, 1987

[54] SUBSTITUTED TRANS-1,2-DIAMINOCYCLOHEXYL AMIDE COMPOUNDS

[75] Inventor: David C. Horwell, Foxton, England

[73] Assignee: Warner-Lambert Company, Morris Plains, N.J.

[21] Appl. No.: 844,058

[22] Filed: Mar. 26, 1986

Related U.S. Application Data

[60] Division of Ser. No. 669,921, Nov. 13, 1984, Pat. No. 4,598,087, which is a continuation-in-part of Ser. No. 558,737, Dec. 6, 1983, abandoned.

[51] Int. Cl.$^4$ .................. A61K 31/165; C07C 103/75
[52] U.S. Cl. ..................................... 514/622; 564/175
[58] Field of Search ......................... 514/622; 564/175

[56] References Cited

U.S. PATENT DOCUMENTS

4,098,904  7/1978  Szmuszkovicz ..................... 548/578
4,212,878  7/1980  Lednicer et al. ............... 514/622 X
4,359,476  11/1982  Kaplan et al. ................. 546/234 X Primary Examiner—Joseph Paul Brust
Attorney, Agent, or Firm—Jerry F. Janssen

[57] ABSTRACT

Substituted trans-1,2-diaminocyclohexyl amide compounds demonstrating selective opioid receptor binding possess utility as analgesic, diuretic, and psychotherapeutic agents. A method of preparing the compounds, pharmaceutical compositions employing the compounds, and a method of alleviating pain employing the compounds are also disclosed.

4 Claims, No Drawings

SUBSTITUTED TRANS-1,2-DIAMINOCYCLOHEXYL AMIDE COMPOUNDS

CROSS-REFERENCE TO RELATED APPLICATIONS

This application is a divisional of application Ser. No. 669,921 filed Nov. 13, 1984 (now U.S. Pat. No. 4,598,087 issued July 1, 1986) which is a continuation-in-part of application Ser. No. 558,737 filed Dec. 6, 1983 (now abandoned).

BACKGROUND OF THE INVENTION

The search for strong analgesics which also possess minimal potential for dependency has been among the highest priority efforts in pharmacological research. These research efforts have, to a great extent, involved chemical modifications of the opiate structure and the discovery of chemically novel compounds which possess morphine-like activity.

The discovery of endogenous opioids has led workers in the field to consider that these peptides, possessing less rigid structures, might interact with opioid receptors other than those to which the classical rigid structure opiates, such as morphine, bind.

The concept of multiple opioid receptors has been supported by studies with nalorphine and a series of benzomorphans which display unusual pharmacological properties dissimilar from morphine, yet blocked by the selective opioid antagonists. [See, for example, W. R. Martin, et al., *J. Pharmacol. Exp. Ther.*, 197: 517–532 (1976)].

The existence of multiple types of opioid receptors is of importance because it suggests the possibility of separating the desirable analgesic and psychotherapeutic effects of a drug compound from the undesirable abuse potential or habituating effects.

U.S. Pat. No. 4,145,435 describes certain 2-aminocycloaliphatic amide compounds as analgesics. In particular, trans-3,4-dichloro-N-methyl-N-[2-(1-pyrrolidinyl)-cyclohexyl]-benzacetamide has been reported to possess selective kappa agonist activity, and therefore to possess analgesic activity without attendant dependence liability. [See P. V. Vanvoigtlander, et al., *J. Pharmacol. Exp. Iher.*, =224: 7–12 (1983)].

Recently, the diuretic effect of various opioid agonists and antagonists has been studied, and it has been shown that kappa agonists tend to increase urination, while mu agonists decreased urination. [See J. D. Leander, *J. Pharmacol. Exp. Ther.*, 227:35–41 (1983)]. These findings suggest that selective opioid agonists and antagonists also possess potential as diuretics.

SUMMARY OF THE INVENTION

The present invention relates to substituted trans-1,2-diamino-cyclohexylamide compounds useful as analgesics, diuretics, and psychotherapeutic agents. The invention is also concerned with a method of preparing such compounds, pharmaceutical compositions including such compounds, and with a method of alleviating pain in a mammal by administering an effective amount of a pharmaceutical composition in accordance with the present invention.

In its broadest aspect, the present invention encompasses compounds having structural formula I

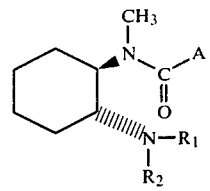

where $R_1$ is methyl and $R_2$ is hydrogen, alkyl of from one to six carbon atoms,

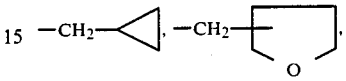

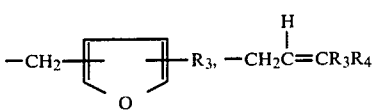

where $R_3$ and $R_4$ are independently hydrogen or methyl, or where $R_1$ and $R_2$ taken together with the nitrogen atom to which they are attached form a ring denoted by

where m is an integer of from three to eight; and wherein A is

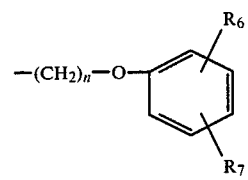

where n is an integer of from one to six; X is oxygen, sulfur, $NR_5$ where $R_5$ is hydrogen or alkyl of from one to six carbon atoms; and $R_6$ and $R_7$ are independently hydrogen, fluorine, chlorine, bromine, nitro, trifluoromethyl, alkyl or from one to six carbon atoms, alkoxy of from one to six carbon atoms, or aryl; and the pharmaceutically accetable acid addition salts thereof.

Also contemplated as falling within this aspect of the present invention at the $N^1$-oxides of compounds having structural formula Ia above. The meaning of the term "$N^1$-oxides" is made clear by referring to structural formula Ia below in which the nitrogen atoms have been numbered. The alkyl-substituted nitrogen atom is numbered "1" and the amido-nitrogen atom is numbered "2"

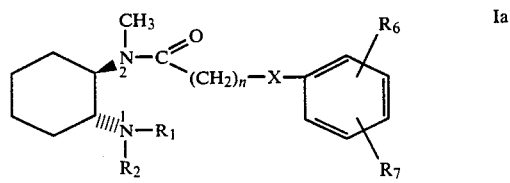

Oxidation of compounds of structural formula I above with, for example, m-chloroperbenzoic acid or other suitable oxidizing agents, readily converts the more basic alkyl-substituted nitrogen atom attached to the cyclohexane ring to its corresponding N-oxide. Throughout this specification and the appended claims, the term "$N^1$-oxide" is meant to refer to these compounds.

In accordance with a second aspect of the present invention, a method of preparing compounds having structural formula I comprises reaching a substituted trans-cyclohexyldiamine of structure II

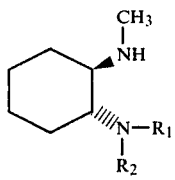

with a substituted carboxylic acid of structural formula III.

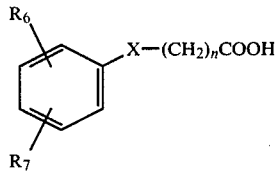

In accordance with another aspect of the present invention, pharmaceutical compositions useful for the alleviation of pain in a mammal comprise an effective amount of a compound having structural formula I above, in combination with a pharmaceutically acceptable carrier.

In a further aspect of the present invention, a method of alleviating pain in a mammal comprises administering to a mammal suffering from pain an effective amount of a pharmaceutical composition, preferably in unit dosage form, which composition includes a compound having structural formula I, above, in combination with a pharmaceutically acceptable carrier.

DETAILED DESCRIPTION

Compounds of the present invention comprise a class of derivatives of trans-1,2-diaminocyclohexane in which one nitrogen is a tertiary amine nitrogen substituted with methyl and a substituent selected from the group $R_2$ as defined above or, preferably is a tertiary amine nitrogen attached to the cyclohexane ring and which is part of a pyrrolidinyl or piperidinyl group. The other nitrogen atom of the 1,2-diaminocyclohexane is an N-methyl amide nitrogen.

By the term "alkyl of from one to six carbon atoms" as used throughout this specification and the appended claims is meant branched or unbranched saturated hydrocarbon groupings containing one to six carbon atoms. Examples include methyl, ethyl, n-propyl, iso-propyl, n-butyl, sec-butyl, iso-butyl, n-pentyl, and the like.

By the term "aryl" is meant phenyl; phenyl substituted with fluorine, chlorine, alkyl of from one to six carbon atoms, alkoxy of from one to six carbon atoms, nitro, and trifluoromethyl; thienyl; and thienyl substituted with alkyl of from one to six carbon atoms, and alkoxy of from one to six carbon atoms.

By the term "alkoxy" is meant a branched or unbranched hydrocarbon grouping such as "alkyl" as defined above, attached to an oxygen atom.

Compounds of the present invention may contain one or more asymmetric carbon atoms and thus exist as enantiomers or diastereomers. The present invention contemplates all possible optical isomeric forms of structural formula I given above. Individual enantiomorphic or diastereomeric forms of the compounds of this invention may be obtained from mixtures by known methods of resolution.

In a preferred embodiment, compounds of formula I are those wherein n is one.

In another preferred embodiment, compounds of the present invention correspond to structural formula I in which m is four or five.

In another preferred embodiment, compounds of formula I are those wherein X is oxygen or sulfur.

In yet another preferred embodiment, compounds of formula I are those wherein $R_6$ and $R_7$ are independently hydrogen, chlorine, fluorine, or nitro.

Specific examples of compounds contemplated as falling within the scope of the present invention are the following:

Trans-2-(2,3-dichlorophenoxy)-1N-methyl-N-[2-(1-pyrrolidinyl)cyclohexyl]acetamide.
Trans-2-(3,4-dichlorophenoxy)-N-methyl-N-[2-(1-pyrrolidinyl)cyclohexyl]acetamide.
Trans-2-(2,4-dichlorophenoxy)-N-methyl-N-[2-(1-pyrrolidinyl)cyclohexyl]acetamide.
Trans-2-(2,6-dichlorophenoxy)-N-methyl-N-methyl-[2-(1-pyrrolidinyl)cyclohexyl]acetamide.
Trans-2-(3-chlorophenoxy)-N-methyl-N-[2-(1-pyrrolidinyl)cyclohexyl]acetamide.
Trans-N-methyl-2-(phenylthio)-N-[2-(1-pyrrolidinyl)-cyclohexyl]acetamide.
Trans-2-(2-chlorophenoxy)-N-methyl-N-[2-(1-pyrrolidinyl)cyclohexyl]acetamide.
Trans-2-(4-fluorophenoxy)-N-methyl-N-[2-(1-pyrrolidinyl)cyclohexyl]acetamide.
Trans-N-methyl-2-(2-nitrophenoxy)-N-[2-(1-pyrrolidinyl)cyclohexyl]acetamide.
Trans-N-methyl-2-phenoxy-N-[2-(1-pyrrolidinyl)cyclohexyl]-acetamide.
Trans-N-methyl-2-(3-methylphenoxy)-N-[2-(1-pyrrolidinyl)-cyclohexyl]acetamide.
Trans-N-methyl-2-(4-methylphenoxy)-N-[2-(1-pyrrolidinyl)cyclohexyl]acetamide.
Trans-2-(4-methoxyphenoxy)-N-methyl-N-[2-(1-pyrrolidinyl)cyclohexyl]acetamide.
Trans-2-(2-methoxyphenoxy)-N-methyl-N-[2-(1-pyrrolidinyl)cyclohexyl]acetamide.
Trans-2-[4-(1,1-dimethylethyl)phenoxy]-N-methyl-N-[2-(1-pyrrolidinyl)cyclohexyl]acetamide.
Trans-2-[(4-chlorophenyl)thio]-N-methyl-N-[2-(1-pyrrolidinyl)cyclohexyl]acetamide.
Trans-2-(2,6-dichlorophenoxy)-N-methyl-N-[2-(methylamino)cyclohexyl]acetamide.
Trans-4-(2,4-dichlorophenoxy)-N-methyl-N-[2-(methylamino)cyclohexyl]butanamide.
Trans-methyl-2-(phenylamino)-N-2-(1-pyrrolidinyl)cyclohexyl]acetamide.
Trans-2-([1,1-biphenyl]-4-yloxy)-N-methyl-N-2-(1-pyrrolinyl)cyclohexyl]acetamide.
Trans-4-(2,4-dichlorophenoxy)-N-methyl-N-[2-(1-pyrrolidinyl)cyclohexyl]butanamide.

In general, compounds of the present invention are prepared by reacting the appropriate trans-1,2-diaminocyclohexane of structural formula II

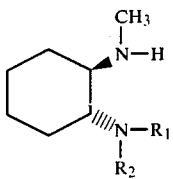

with a carboxylic acid of structural formula III

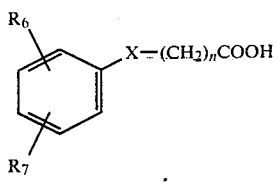

or a reactive derivative formed from such a carboxylic acid.

The appropriate carboxylic acid (III) may be reacted directly with the amine with the aid of such reagents as dicyclohexylcarbodiimide and the like. Alternatively, the carboxylic acids are first converted to a reactive derivative such as an activated ester, anhydride, acid halide such as the bromide or chloride, or acyl imidazoles of the formula IV

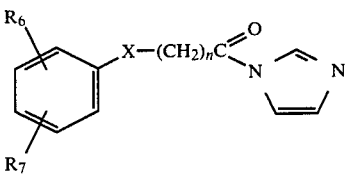

and the resulting carboxylic acid derivative reacted with the substituted trans-1,2-diaminocyclohexane (II).

For example the reaction between the cyclic diamine (II) and the appropriate carboxylic acid (III) is carried out in the presence of the coupling reagent, dicyclohexylcarbodiimide, in a cyclic ether solvent such as tetrahydrofuran or dioxane until the desired product is formed. The reaction will generally proceed at ambient temperatures but, depending upon the reactivity of the specific materials involved, the desired reaction time, the solvent being employed, and the molar proportions of reagents, the reaction temperature may be varied between about −25° C. and the reflux temperature of the solvent employed.

The reaction between the acid halide and the cyclic diamine (II) is carried out, generally at ambient temperature, in a suitable solvent in the presence of an acid acceptor such as a tertiary amine or an alkali metal or alkaline earth metal carbonate or bicarbonate. The mixture of the amine and the acid halide is allowed to stand until reaction is complete.

When the reaction between the cyclic diamine (II) and the acid (III) or acid derivative has proceeded to substantial completion, the desired product is recovered from the reaction mixture by techniques well known to practitioners of the organic chemical arts.

For example, the reaction mixture can be evaporated under vacuum, if desired, to remove the solvent and other volatile components of the reaction mixture to yield the product, generally as an oil. This residual material is then taken up in a solvent such as diethyl ether, washed first with a salt solution such as sodium bicarbonate solution and then with water. Separation of the organic phase, drying over, for example anhydrous magnesium sulfate, and evaporation of the ether solvent, yields the desired product, usually as an oil or crystalline solid.

The starting trans-1,2-diaminocyclohexane compounds of the present invention are prepared by the method detailed in U.S. Pat. No. 4,145,435. The carboxylic acids (III) are known, or if novel, are prepared by reaction sequences well known in the art. The acyl imidazole derivatives (IV) of the carboxylic acids are prepared by reacting carbonyldiimidazole with the appropriate acid.

The free base form of the compounds of this invention are readily converted, if desired, by known methods to the acid addition salts by reaction with any of a number of inorganic or organic acids including hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, and related acids and mixtures thereof. The free base form of the compounds of the present invention and the acid addition salt may differ in certain of their physical properties, such as solubility in polar solvents, but are otherwise equivalent for the purposes of this invention.

The compounds of the present invention possess significant analgesic activity with potential for minimum dependence liability due to their selective kappa opioid receptor binding properties. In addition to analgesics, selective kappa agonists also cause opioid receptor-mediated sedation, diuresis, and corticosteroid elevations. Accordingly, the compounds of the present invention may also be useful diuretics and psychotherapeutic agents as well as analgesics.

Representative examples of the compounds of formula I have shown positive activity in standard laboratory analgesic tests in animals such as mice. For example, mice showed longer tolerance, greater than 20 seconds, (maximum determined at 40 seconds from control) on a hot plate at 55° C. when given subcutaneously the compound of Example 1 at 100 mg/kg of animal body weight. When compared with control, mice also exhibited less writhing induced by acetylcholine when given subcutaneous doses of 20 and 200 mg/kg of the compound of Example 1.

Representative examples of the compounds of the present invention, when tested in vitro to determine the extent of opioid receptor binding, were found to be selectively bound to the kappa receptors with evidence of little or no binding to the mu and delta receptors. The benefits of this selective binding has already been mentioned above and is also described by M. B. Tyers, *Br. J. Pharmac.* (1980) 69:503–512.

Measurement of the kappa opioid receptor site binding activity of compounds of the present invention was made by the following method. Guinea pig braing homogenates were prepared fresh each day utilizing the method of Gillan, et al, *Br. J. Pharm.*, 70:481–490 (1980).

The binding of tritiated etorphine to brain homogenates was measured in the presence of unlabelled competitor compounds of the present invention with 200 nanomolar D-Ala-D-Leu-enkephalin (acronym DA- DLE) and 200 nanomolar D-Ala-MePheGly-ol-enkephalin (acronym DAGO) added to saturate the delta and mu opioid receptors, respectively. The reaction was terminated by rapid filtration and the radioactivity bound to the filters counted by liquid scintillation spectrophotometry.

Measurement of the mu and delta opioid receptor site binding activity of compounds of the present invention was made by the following method. Guinea pig homogenates were prepared fresh each day utilizing the method of Gillan, et al, cited above.

Homogenates were incubated for 150 minutes at 0° C. with either tritiated DAGO to measure mu receptor site binding activity, or with tritiated DADLE in the presence of a ten-fold excess of unlabelled DAGO to measure delta opioid receptor site activity. Nonspecific binding was determined in the presence of $10^{-6}$ M DAGO and $10^{-6}$ M DADLE.

Reactions were terminated by rapid filtration and the radioactivity bound to the filters counted by liquid scintillation spectrophotometry.

Data was analyzed by the methods of Scatchard, *Ann. N.Y. Acad. Sci.*, 51:660–672 (1949) and Hill, *J. Physiol.*, 40:IV–VIII (1910). The inhibition of binding of tritriated etorphine, DAGO and DADLE by cold ligands was determined from the regression of log percentage inhibition of specific binding or log concentration of cold ligand. The inhibition constant ($K_i$) was calculated from the equation:

$$K_i = \frac{IC_{50}}{1 + [L]/KD}$$

where [L] is the concentration of the labelled ligand and $K_D$, its equilibrium dissociation constant.

The results of these tests for several representative compounds of the present invention are presented in Table 1.

TABLE 1

| R1 R2 | n | x | R6, R7 | ($K_i$ M) Kappa | Mu |
|---|---|---|---|---|---|
| Pyrrolidinyl | 1 | O | 4-Cl, H | $9.2 \times 10^{-7}$ | $>>10^{-5}$ |
| Pyrrolidinyl | 1 | O | 2,3-di Cl | $10^{-7}$–$10^{-8}$ | $>10^{-6}$ |
| Pyrrolidinyl | 1 | O | 3,4-di Cl | $3.48 \times 10^{-8}$ | $6.21 \times 10^{-7}$ |
| Pyrrolidinyl | 1 | O | 2,4-di Cl | $1.71 \times 10^{-7}$ | $>10^{-6}$ |
| Pyrrolidinyl | 1 | S | H, H | $\sim 10^{-6}$ | $>>10^{-6}$ |
| Pyrrolidinyl | 1 | O | 4-F, H | $1.16 \times 10^{-7}$ | $4.03 \times 10^{-6}$ |
| Pyrrolidinyl | 1 | O | 3-Cl, H | $9.25 \times 10^{-8}$ | $1.38 \times 10^{-6}$ |
| Pyrrolidinyl | 1 | O | 2,6-di Cl | $2.14 \times 10^{-6}$ | $3.96 \times 10^{-6}$ |
| Pyrrolidinyl | 1 | O | 4-OCH3 | $>10^{-6}$ | $>>10^{-6}$ |
| Pyrrolidinyl | 1 | O | H, H | $\sim 10^{-6}$ | $>>10^{-6}$ |
| Pyrrolidinyl | 1 | O | 2-Cl, H | $1.99 \times 10^{-7}$ | $>>10^{-6}$ |
| Pyrrolidinyl | 1 | O | 4-CH3, H | $8.63 \times 10^{-7}$ | $3.33 \times 10^{-6}$ |
| Pyrrolidinyl | 1 | O | 2-NO2, H | $2.21 \times 10^{-7}$ | $5.13 \times 10^{-6}$ |
| Pyrrolidinyl | 1 | O | 3-CH3, H | $1.42 \times 10^{-7}$ | $>10^{-6}$ |
| Pyrrolidinyl | 1 | O | 2-OCH3, H | $7.17 \times 10^{-8}$ | $>10^{-6}$ |
| Pyrrolidinyl | 1 | O | 4-tBu, H | $2.61 \times 10^{-7}$ | $1.96 \times 10^{-7}$ |
| Pyrrolidinyl | 1 | S | 4-Cl, H | $1.0 \times 10^{-6}$ | $2.8 \times 10^{-6}$ |
| Pyrrolidinyl | 2 | O | 4-Cl, H | $>10^{-6}$ | NT |
| CH3, H | 1 | O | 2,6-di Cl | $\sim 10^{-5}$ | $\sim 10^{-5}$ |
| c-C4H8 | 3 | O | 2,4-di Cl | $\sim 10^{-5}$ | $\sim 10^{-5}$ |
| CH3, H | 3 | O | 2,4-di Cl | $\sim 10^{-5}$ | NT |
| CH3, CH2CH·CH2 | 3 | O | 2,4-di Cl | $\sim 10^{-5}$ | NT |
| c-C4H8 | 1 | N | H, H | $8.26 \times 10^{-7}$ | $\sim 10^{-5}$ |

The compounds of the present invention, and/or the nontoxic, pharmaceutically acceptable salts thereof, may be administered to mammals in pharmaceutical compositions or formulations which comprise one or more of the compounds of this invention and/or the nontoxic, pharmaceutically acceptable, nontoxic carrier.

The compounds of this invention may be administered parenterally in combination with conventional injectable liquid carriers such as sterile pyrogenfree water, sterile peroxide-free ethyl oleate, dehydrated alcohols, propylene glycol, and mixtures thereof.

Suitable pharmaceutical adjuvants for the injecting solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

Compounds of the present invention, and/or the nontoxic, pharmaceutically acceptable salts thereof, may be administered to mammals orally in combination with conventionally compatible carriers in solid or in liquid form. These oral pharmaceutical compositions may contain conventional ingredients such as binding agents selected form the group consisting of syrups, acacia, gelatin, sorbitol, tragacanth, polyvinylpyyrolidone, and mixtures thereof. The compositions may further include fillers such as lactose, mannitols, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid silica, or agents to facilitate disintegration of the solid formulation, such as starch, and wetting agents such as sodium lauryl sulfate.

The oral pharmaceutical compositions may take any convenient form such as tablets, capsule, lozenges, aqueous or oily suspensions, emulsions, or even dry powders which may be reconstituted with water and/or other liquid media prior to use.

Compounds of the present invention and/or the non-toxic, pharmaceutically acceptable salts thereof may be administered topically in the form of an ointment or cream containing from about 0.1% to 10% by weight of the active component in a pharmaceutical ointment or cream base.

Compounds of the present invention and/or the nontoxic, pharmaceutically acceptable salts thereof, may be administered to mammals rectally in the form of suppositories. For preparing suppositories, a low-melting wax such as a mixture of fatty acid glycerides or cocoa butter is first melted, and the active ingredient is dispersed homogeneously therein by stirring. The molten homogeneous mixture is then poured into convenient sized molds, allowed to cool and thereby solidify.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may optionally be encapsulated in, for example, gelatin capsules, in an effective amount.

Preferably, the pharmaceutical compositions of this invention are in unit·dosage form. In such form, the preparation is subdivided into unit doses containing appropriate amounts of the active component. Ihe unit doses form can be a packaged preparation with the package containing discrete quantities of the preparation. For example, the package may take the form of packeted tablets, capsules, and powders in envelopes, vials or ampoules. The unit dosage form can also be a capsule, cachet, or tablet itself or can be the appropriate number of any of these packaged forms.

The quantity of active compound in a unit dose of preparation may be varied or adjusted from 0.5 mg to about 350 mg according to the particular application and the potency of the active ingredient.

When employed systematically in therapeutic use as analgesic agents in the pharmaceutical method of this invention, the compounds are administered at doses of about 0.05 mg to 2.0 mg of active compound per kilogram of body weight of the recipient.

The following examples are provided to enable one skilled in the art to practice the present invention. The examples are not to be read as limiting the scope of the invention as defined by the appended claims, but as merely illustrative thereof.

GENERAL SYNTHETIC METHODS

Preparation of amide monohydrochlorides (2 mmol scale)

Method A: Trans-N-methyl-2-(1-pyrrolidinyl) cyclohexanamine (364 mg, 2 mmol) in methylene chloride (5 ml) was added with stirring to a solution of the acid chloride [prepared by the action of thionyl chloride (5 ml) on the appropriate carboxylic acid (2 mmol)] in methylene chloride (20 ml). After stirring for ten minutes, the mixture was evaporated to small volume and diethyl ether added until no more precipitate appeared. The product was collected by filtration, washed with diethyl ether, and dried in a vacuum oven at 70° C. overnight.

Method B: Trans-N-methyl-2-(1-pyrrolidinyl)cyclohexanamine (364 mg, 2 mmol) in methylene chloride (5 ml) was added with stirring to a solution of the acid chloride [prepared by the action of thionyl chloride (5 ml) on the appropriate carboxylic acid (2 mmol)]in a 1:1 mixture of methylene chloride and diethyl ether (20 ml). After stirring for ten minutes, diethyl ether was added until no more precipitate appeared. The product was collected by filtration, washed with diethyl ether, and dried in a vacuum oven at 70° C. overnight.

Method C: A solution of carbonyl di-imidazole (356 mg, 2.2 mmol) in dry tetrahydrofuran (10 ml) was added to a solution of the appropriate carboxylic acid (2 mmol) in tetrahydrofuran (20 ml). The mixture was stirred for 30 minutes at room temperature. Trans-N-methyl-2-(1-pyrrolidinyl)cyclohexanamine (364 mg, 2 mmol) in tetrahydrofuran (10 ml) was added, the mixture heated to reflux, then stirred at room temperature for 16 hours. The reaction was evaporated to small volume, and the residue dissolved in ethyl acetate (100 ml). The extract was washed with saturated sodium bicarbonate (3×50 ml), then water (50 ml), dried (MgSO$_4$), and evaporated under reduced pressure.

Method D: Substantially as described in Method C with the exception that the mixture of reactants was stirred at ambient temperature for 16 hours rather than being heated under reflux.

EXAMPLE 1

Preparation of trans-2-(4-chlorophenoxy)-N-methyl-N-[2-(1-pyrrolidinyl)cyclohexyl]acetamide A. Preparation of 7-methyl-7-azabicyclo[4.1.0]heptane [Modification of method of T. Taguchi and M. Eto, *J. Amer. Chem. Soc.* 80, 4076 (1958)].

i. Cyclohexene oxide (Aldrich, 196.3 g 2M) was added to a 25/30% solution of aqueous methylamine (745 ml, 6M) (25% solution) dropwise with stirring and cooling in an icebath over one hour, during which time the temperature reached 46° C. The solution was stirred at room temperature overnight, and then refluxed for three hours in fume hood. The solution was cooled in an icebath and saturated with solid NaOH, extracted with 4×200 ml ether, dried (MgSO$_4$) and evaporated to dryness on rotary evaporator.

The crude product, trans-2-(methylamino)cyclohexanol, was distilled under water vacuum pressure, the first small sample of cyclohexene epoxide discarded. The bulk was distilled from a 1-liter flask with a 60W isomantle and a short Leibig condenser over a two hour period to yield the product.

bp: 118° C. (water vacuum)

yield: 208 g (81%)

ii. Trans-2-(methylamino)cyclohexanol (208 g, 1.61 M) was placed in a three liter beaker and dissolved in ether (400 ml). Chlorosulphonic acid (1.89 g, 1.62 M) was added dropwise to the ice-salt cooled solution. Added a further 200 ml of ether. The solution was hand stirred. Addition took one hour. The solution/solid was allowed to warm to room temperature and stand for three hours. The ether was decanted and the white salt washed with 300 ml ether which was also decanted.

The solid was cooled in ice-salt bath and NaOH (218 g in one liter of water) added slowly. The thick white solid was left at room temperature overnight.

The crude product, 7-methyl-7-azabicyclo[4.1.0] heptane, was distilled in isomantle with continuous addition of water from separating funnel to retain approximately original volume. After 600 ml of liquid had been collected, the total distillate was saturated with solid NaOH, extracted with 5×200 ml ether, dried (MgSO$_4$) and evaporated on rotary evaporator.

The product was distilled using a water vacuum and air bleed, the collection vessel being cooled in an ice bath.

yield: 67 g (37%), b.p. 38° C. (water vacuum and bleed)

iii. Preparation of trans-N-methyl-2-(1-pyrrolidinyl)cyclohexanamine

A mixture of 7-methyl-7-azabicyclo[4.1.0] heptane (7.0 g, 0.063 M), pyrrolidine (17.92 g, 0.25 M), water (10 ml) and ammonium chloride (0.16 g) was stirred and refluxed for 21 hours. The solution was cooled and solid sodium hydroxide added and extracted with ether (3×50 ml). The extracts were dried over magnesium sulphate and evaporated under reduced pressure to a brown oil. This was distilled under high vacuum to yield a colorless oil.

bp: 95° C. (6.0 g)

B. Preparation of trans-2-(4-chlorophenoxy)-N-methyl-N-[2-(1-pyrrolidinyl)cyclohexyl]acetamide, hydrochloride.

Trans-N-Methyl-2-(1-pyrrolidinyl)cyclohexanamine (0.182 g) was dissolved in methylene chloride (10 ml) and stirred at room temperature. The acid chloride of 4-chlorophenoxyacetic acid (0.205 g) dissolved in methylene chloride (10 ml) was added and let stand for 12 hours. Ether was added to rapidly stirred solution until no more precipitate appeared. After further rapid stirring for one hour, the precipitate was filtered and dried in a vacuum oven at 90° C. for one hour, and stored in a predried bottle. The product was in the form of white needles (360 mg) mp 184°–186° C.

EXAMPLE 2

Trans-(±)-2-(2,3 dichlorophenoxy)-N-methyl-N-[2-(1-pyrrolidinyl)cyclohexyl]acetamide monohydrochloride By Method A, 2,3-dichlorophenoxyacetic (442 mg, 2 mmol) was converted to the amide monohydrochloride (753 mg, 89%); VmaxC=0 1665 cm$^{-1}$.

EXAMPLE 3

Trans-(±)-2-(2,4-dichlorophenoxy)-N-methyl-N-[2-(1-pyrrolidinyl)cyclohexyl]acetamide monohydrochloride By Method A, 2,4-dichlorophenoxyacetic acid (442 mg, 2 mmol) was converted to the amide monohydrochloride (701 mg, 83%); VmaxC—0 1670 cm$^{-1}$.

EXAMPLE 4

Trans-(±)-N-methyl-2(phenylthio)-N-[2-(1-pyrrolidinyl)cyclohexyl]acetamide monohydrochloride By Method A, phenylthioacetic acid (336 mg, 2 mmol) was converted to the amide monohydrochloride (552 mg, 75%); VmaxC=0 1650 cm$^{-1}$.

EXAMPLE 5

Trans-(±)-2-(4-fluorophenoxy)-N-methyl-N-[2-(1pyrrolidinyl)cyclohexyl]acetamide monohydrochloride By Method A, 4-fluorophenoxyacetic acid (340 mg, 2 mmol) was converted to the amide monohydrochloride (656 mg, 89%); VmaxC=0 1660 cm$^{-1}$.

EXAMPLE 6

Trans-(±)-2-(3-chlorophenoxy)-N-methyl-N-[2-(1pyrrolidinyl)cyclohexyl]acetamide monohydrochloride By Method B, 3-chlorophenoxyacetic acid (1.49 g, 8 mmol) was converted to the amide monohydrochloride (2.89 g, 93%); VmaxC=0 1655 cm$^{-1}$.

EXAMPLE 7

Trans(±)-2-(2,6-dichlorophenoxy)-N-methyl-N-[2-(1-pyrrolidinyl)cyclohexyl]acetamide monohydrochloride By Method A, 2,6-dichlorophenoxyacetic acid (3.32 g, 15 mmol) was converted to the amide monohydrochloride (5.74 g, 91%); VmaxC=0 1640 cm$^{-1}$.

EXAMPLE 8

Trans-(±)-2-(4-methoxyphenoxy)-N-methyl-N-[2-(1pyrrolidinyl)cyclohexyl]acetamide monohydrochloride By Method A, 4-methoxyphenoxyacetic acid (364 mg, 2 mmol) was converted to the amide monohydrochloride (707 mg, 92%); VmaxC =0 1665 cm$^{-1}$.

EXAMPLE 9

Trans-(±)-N-methyl-2-phenoxy-N [2-(1-pyrrolidinyl)cyclohexyl]acetamide monohydrochloride Trans-(±)-N-methyl-2-(1-pyrrolidinyl)cyclohexanamine (364 mg, 2 mmol) in methylene chloride (5 ml) was added with stirring to a solution of phenoxyacetyl chloride (341 mg, 2 mmol) in methylene chloride (20 ml). After stirring for five minutes, the mixture was evaporated to small volume and diethyl ether added until no more precipitate appeared. The product was collected by filtration, washed with diethyl ether, and dried in a vacuum oven at 70° C. overnight, to give the amide monohydrochloride (645 mg, 91%); VmaxC=0 1660 cm$^{-1}$.

EXAMPLE 10

Trans-(±)-2-(2-chlorophenoxy)-N-methyl-N-[2-(1pyrrolidinyl)cyclohexyl]acetamide monohydrochloride By Method A, 2-chlorophenoxyacetic 373 mg, 2 mmol) was converted to the amide monohydrochloride (689 mg, 89%); VmaxC=0 1660 cm$^{-1}$.

EXAMPLE 11

Trans-(±)-N-methyl-2-(4-methylphenoxy)-N-[2-(1pyrrolidinyl)cyclohexyl]acetamide monohydrochloride By Method A, 4-methylphenoxyacetic acid (332 mg, 2 mmol) was converted to the amide monohydrochloride (591 mg, 81%); VmaxC=0 1660 cm$^{-1}$.

EXAMPLE 12

Trans-(±)-N-methyl-2-(2-nitrophenoxy)-N-[2-(1-pyrrolidinyl)cyclohexyl]acetamide monohydrochloride By method A, 2-nitrophenoxyacetic acid (394 mg, 2 mmol) was converted to the amide monohydrochloride (694 mg, 87%); VmaxC=0 1660 cm$^{-1}$.

EXAMPLE 13

Trans-(±)-2-(2-methoxyphenoxy)-N-methyl-N-[2-(1-pyrrolidinyl)cyclohexyl]acetamide monohydrochloride By Method A, 2-methoxyphenoxyacetic acid (364 mg, 2 mmol) was converted to the amide monohydrochloride (696 mg, 91%); VmaxC=0 1660 cm$^{-1}$.

EXAMPLE 14

Trans-(±)-2-[4-(1,1-dimethylethyl)pheonxy]-N-methyl-N-[2-(1-pyrrolidinyl)cyclohexyl]acetamide monohydrochloride By Method A, 4-(1,1-dimethylethyl)phenoxy acetic acid (312 mg, 1.5 mmol) was converted to the amide monohydrochloride (469 mg, 77%); VmaxC=0 1660 cm$^{-1}$.

EXAMPLE 15

Trans-(±)-2-[(4-chlorophenyl)thio]-N-methyl-N-[2-(1-pyrrolidinyl)cyclohexyl]acetamide monohydrochloride By Method A, (4-chlorophenyl)thioacetic acid (202.5 mg, 1 mmol) was converted to the amide monohydrochloride (304 mg, 75%); VmaxC=0 1650 cm$^{-1}$.

EXAMPLE 16

Trans-(±)-3-(4-chlorophenoxy)-N-methyl-N-[2-(1-pyrrolidinyl)cyclohexyl]propanamide monohydrochloride By Method A, 3-(4-chlorophenoxy)propanoic acid (401 mg, 2 mmol) was converted to the amide monohydrochloride (484 mg, 60%); VmaxC=0 1635 cm$^{-1}$.

EXAMPLE 17

Trans-(±)-4-(2,4-dichlorophenoxy)-N-methyl-N-[2-(1-pyrrolidinyl)cyclohexyl]butanamide monohydrochloride By Method B, 4-(2,4-dichlorophenoxy)butanoic acid (498 mg, 2 mmol) was converted to the amide monohydrochloride (685 mg, 76%); VmaxC=0 1635 cm$^{-1}$.

EXAMPLE 18

Trans-(±)-N-methyl-2-(phenylamino)-N-[2-(1-pyrrolidinyl)cyclohexyl]acetamide

By Method D, 2-phenylaminoacetic acid (755 mg, 5 mmol) was converted to the amide. The product was recrystalized from hexane/methylene chloride to yield trans-(±)-N-methyl-2-(phenylamino)-N-[2-(1-pyrrolidinyl)cyclohexyl]acetamide (1.03 g, 65%); VmaxC=0 1635 cm$^{-1}$.

EXAMPLE 19

Trans-(±)-N-methyl-2-(4-phenylphenoxy)-N-[2-(1-pyrrolidinyl)cyclohexyl]acetamide monohydrochloride By Method B, 4-phenylphenoxyacetic acid (228 mg, 1 mmol) was converted to the amide monohydrochloride (382 mg, 89%); VmaxC=0 1660 cm$^{-1}$.

EXAMPLE 20

Trans-(±)-2-(2,6-dichlorophenoxy)-N-methyl-N-[2-(methylamino)cyclohexyl]acetamide monohydrochloride 2,6-dichlorophenoxyacetic acid (0.50 g, 2.3 mmol) was treated with thionyl chloride (6 ml) at room temperature for 60 hours. The solution was concentrated in vacuo to give an oil which was dissolved in dichloromethane (2.5 ml) and added dropwise over three minutes to a stirred solution of trans-(±)-N, N'-dimethylcyclohexane-1,2-diamine (0.35 g, 3.1 mmol) in dichloromethane (2.5 ml). After 1.5 hours at room temperature the mixture was filtered and the filtrate treated with diethyl ether until precipitation occurred. The resulting white solid was recrystallized (dichloromethane-diethyl ether) to give trans-(±)-2-(2,6-dichlorophenoxy)-N-methyl-N-[2-(methylamino)cyclohexyl]acetamide monohydrochloride (171 mg, 19%); VmaxC=0 (liquid file) 1655 cm$^{-1}$.

EXAMPLE 21

Trans-(±)-4-(2,4-dichlorophenoxy)-N-methyl-N-[2-(methylamino)cyclohexyl]butanamide monohydrochloride A stirred solution of 4-(2,4-dichlorophenoxy)butyric acid (1.9 g, 7.7 mmol) and carbonyl diimidazole (1.25 g, 7.7 mmol) in tetrahydrofuran (7 ml) was refluxed for 50 minutes then cooled to room temperature and added to a solution of trans-(±)-N,N'-dimethylcyclohexane 1,2-amine (1.0 g, 7.0 mmol) in tetrahydrofuran (7 ml) over 15 minutes. After a further 15 minutes at room temperature the mixture was concentrated in vacuo, poured into saturated aqueous sodium bicarbonate (60 ml) and extracted with dichloromethane-diethyl ether (20 ml), filtered through a plug of cotton wool and treated with a solution of hydrogen chloride in diethyl ether until the solution became acidic. The resulting precipitate was isolated by filtration, washed with diethyl ether and recrystallized (dichloromethane-diethyl ether) to give -trans-(±)-4-(2,4-dichlorophenoxy)-N-methyl-N-[2-(methylamino)cyclohexyl]butanamide monohydrochloride as a white solid (0.44 g, 17%); Vmax (liquid film) 1640 cm$^{-1}$.

EXAMPLE 22

Trans-(±)-4-(2,4-dichlorophenoxy)-N-methyl-N-[2-[methyl(2-propenyl)amino]cyclohexyl]butanamide monohydrochloride A solution of trans-(±)-4-(2,4-dichlorophenoxy)-N-methyl-N-[2-(methylamino)cyclohexyl]butanamide monohydrochloride (0.30 g, 0.73 mmol) in dichloromethane (10 ml) was treated with aqueous potassium carbonate to liberate the parent amine. This oil was dissolved in dimethyl formamide (0.7 ml) and treated with allyl bromide (0.07 ml) and sodium bicarbonate (95 mg) with stirring and heating at 54°-60° for two hours. After concentration in vacuo the residue was poured into saturated aqueous sodium bicarbonate (20 ml) and extracted with dichloromethane (2×20 ml). Silica gel chromatography (70:30:1 ethyl acetate-hexanetriethylamine0 of the residue furnished trans-(>)-4-(2,4-dichlorophenoxy)-N-methyl-N-[2-methyl(2-propenyl)amino]cyclohexyl]butanamide (0.21 g, 70%); VmaxC=0 (liquid film) 1640 cm$^{-1}$. This oil was dissolved in dichloromethane-diethyl ether (20 ml) filtered through a plug of cotton wool and treated with a solution of hydrogen chloride in diethyl ether until the solution became acidic. The resulting precipitate was isolated by filtration, washed with diethyl ether and recrystallized (dichloromethanediethyl ether) to give the hydrochloride as a white solid (160 mg, 70%) mp 148°-152° C.

EXAMPLE 23

Trans-(±)-2-(3,4-dichlorophenoxy)-N-methyl-N-[2-(1-pyrrolidinyl)cyclohexyl]acetamide monohydrochloride By Method A, 3,4-dichlorophenoxyacetic acid (1.105 g, 5 mmol) was converted to the amide monohydrochloride (1.82 g, 86%); VmaxC=0 1655 cm$^{-1}$.

EXAMPLE 24

Trans-(±)-N-methyl-2-(3-(methylphenoxy)-N-[2-(1-pyrrolidinyl)cyclohexyl]acetamide monohydrochloride By Method A, 3-methylphenoxyacetic acid (249 mg, 1.5 mmol) was converted to the amide monohydrochloride 9300 mg, 56%); VmaxC=0 1660 cm$^{-1}$.

I claim:

1. A compound having the structural formula

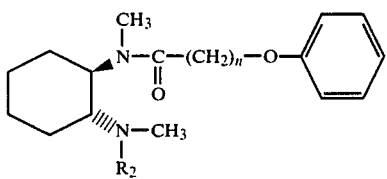

where n is an integer of from 1 to 4; $R_2$ is hydrogen, alkyl of from one to six carbon atoms, or —$CH_2CH=CR_3R_4$ where $R_3$ and $R_4$ are independently hydrogen or methyl; and wherein the phenyl ring may be optionally substituted by one or two, same or diferent, substituents selected from fluorine, chlorine, or bromine.

2. A compound in accordance with claim 1 selected from the group consisting of:
trans-2-(2,6-dichlorophenoxy)-N-methyl-N-acetamide;
trans-4-(2,4-dichlorophenoxy)-N-methyl-N-butanamide;
trans-4-(2,4-dichlorophenoxy)-N-methyl-N-butanamide;
and the pharmaceutically acceptable acid addition salts thereof.

3. A pharmaceutical composition useful for alleviating pain in a mammal, said composition comprising an analgesically effective amount of a compound in accordance with claim 1 in combination with a pharmaceutically acceptable carrier.

4. A method of alleviating pain in a mammal in need of such treatment, said method comprising administering to said mammal an analgesically effective amount of a pharmaceutical composition in accordance with claim 3 in unit dosage form.

* * * * *